United States Patent [19]

Samson

[11] Patent Number: 5,228,452

[45] Date of Patent: Jul. 20, 1993

[54] PROXIMAL END FITTING WITH AN IMPROVED SEAL FOR USE IN A CATHETER GUIDEWIRE ASSEMBLY

[75] Inventor: Gene Samson, Milpitas, Calif.

[73] Assignee: Target Therapeutics Inc., Fremont, Calif.

[21] Appl. No.: 839,317

[22] Filed: Feb. 19, 1992

[51] Int. Cl.$^5$ .............................................. A61B 5/00
[52] U.S. Cl. ..................................... 128/772; 128/657
[58] Field of Search .................. 128/657, 772; 604/95, 604/280

[56] References Cited

U.S. PATENT DOCUMENTS

| | | | |
|---|---|---|---|
| 5,045,061 | 9/1991 | Seifert et al. | 128/772 |
| 5,112,309 | 5/1992 | Bertaud et al. | 128/772 |
| 5,117,839 | 6/1992 | Dance | 128/772 |

Primary Examiner—Max Hindenburg
Attorney, Agent, or Firm—Morrison & Foerster

[57] ABSTRACT

The invention comprises a proximal end fitting for use within a guidewire assembly wherein the proximal end fitting comprises an elongated radially compressible tube. When in use, the tube is compressed against the O-ring seal in the fitting to better facilitate the seal between the O-ring and the guidewire and thereby better control blood reflux.

8 Claims, 2 Drawing Sheets

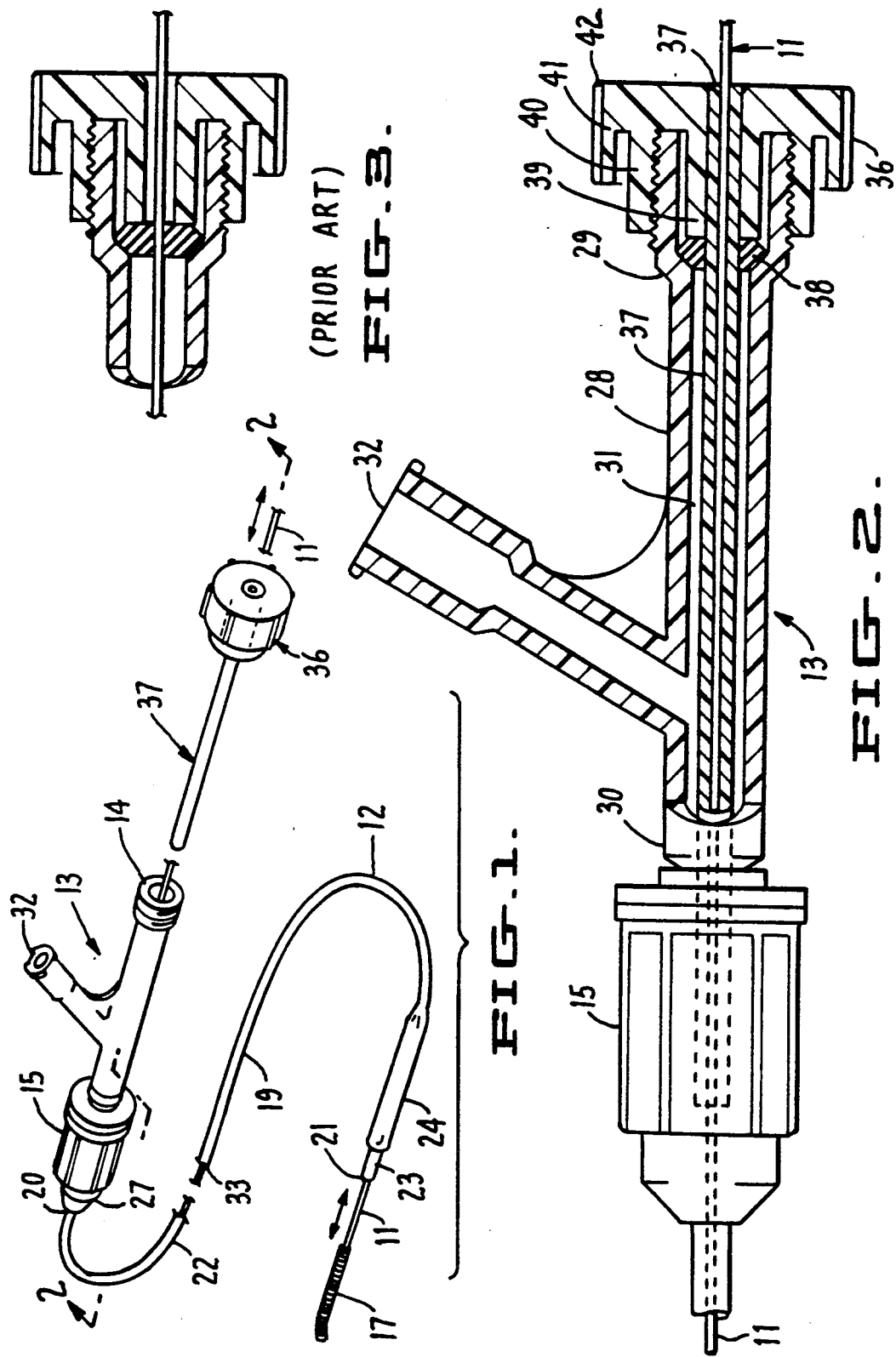

| SAMPLE | 10 PSI | 20 PSI | 30 PSI | 40 PSI | 50 PSI | 60 PSI | 70 PSI | 80 PSI | 90 PSI | 100 PSI | 110 PSI | 120 PSI |
|---|---|---|---|---|---|---|---|---|---|---|---|---|
| #1 | n.l.* | n.l. | n.l. | n.l. | n.l. | n.l. | n.l. | 2 drops | 2 drops | 2 drops | 1 drop | 2 drops |
| #2 | n.l. | n.l. | n.l. | n.l. | n.l. | n.l. | n.l. | 2 drops | 1 drop | 2 drops | 2 drops | 2 drops |
| #3 | n.l. | n.l. | n.l. | n.l. | n.l. | 1 drop | 1 drop | 1 drop | 2 drops | 2 drops | 2 drops | 2 drops |
| #4 | n.l. | n.l. | n.l. | 1 drop | n.l. | 1 drop | 1 drop | 1 drop | 1 drop | 2 drops | 2 drops | 2 drops |
| #5 | n.l. | n.l. | n.l. | n.l. | n.l. | n.l. | 1 drop | 1 drop | 2 drops | 2 drops | 2 drops | 2 drops |
| #6 | n.l. | n.l. | n.l. | n.l. | n.l. | 1 drop | 1 drop | 1 drop | 2 drops | 2 drops | 2 drops | 2 drops |
| #7 | n.l. | n.l. | n.l. | n.l. | n.l. | n.l. | 1 drop | 1 drop | 2 drops | 1 drop | 1 drop | 1 drop |
| #8 | n.l. | n.l. | n.l. | n.l. | n.l. | 1 drop | 1 drop | 1 drop | 2 drops | 2 drops | 1 drop | 1 drop |
| #9 | n.l. | n.l. | n.l. | n.l. | n.l. | n.l. | 1 drop | 1 drop | 1 drop | 1 drop | 2 drops | 2 drops |
| #10 | n.l. | n.l. | n.l. | n.l. | n.l. | n.l. | 1 drop | 1 drop | 1 drop | 1 drop | 2 drops | 2 drops |

* "n.l." means "no leakage."

FIGURE 4

PROXIMAL END FITTING WITH AN IMPROVED SEAL FOR USE IN A CATHETER GUIDEWIRE ASSEMBLY

DESCRIPTION

1. Technical Field

This invention is in the general field of surgical instruments and relates specifically to proximal end fittings. These fittings are used with catheter guidewire assemblies in cardiovascular and endovascular procedures to facilitate the placement of catheters within the vasculature of patients.

2. Background

The general procedure for placing catheters within vessels is to track a guidewire through the vessel to the desired position and advance the catheter over the guidewire. Guidewires are required because the catheters themselves do not have sufficient column strength or torqueability to be able to be tracked or steered through the vessel. See, for instance, U.S. Pat. No. 4,884,579.

Normally, blood pressure within a catheter guidewire assembly is controlled by a compression ring seal made out of rubber or rubber-like material. This method restricts wire movement when the seal is too tight and is inefficient when the seal is too loose. The purpose of the present invention, therefore is to control blood reflux into the catheter while the catheter is being positioned at a predetermined vessel site without impeding guidewire movement. When the device is used in conjunction with a compression ring seal, the guidewire can be captured and higher pressure can be controlled. When the compression ring seal is released, the guidewire movement is unrestricted.

DISCLOSURE OF THE INVENTION

The invention comprises a proximal end fitting for use within a guidewire assembly. An elongated, radially compressible plastic tube is connected through the proximal end fitting such that when a catheter is being positioned at an arterial site, blood reflux will be controlled.

More specifically, the invention comprises an improvement to a conventional proximal end fitting for a guidewire assembly. The conventional fitting comprises a tubular body having a proximal end and a distal end and a lumen between the ends through which a guidewire extends. The distal end contains a fitting for sealingly receiving the proximal end of the catheter. A compressible O-ring is positioned within the lumen, and a coaxially movable means fits into the proximal end of the body such that when it is moved into place, it compresses the O-ring. The O-ring thus forms a seal about the guidewire.

The improvement of the present invention comprises an elongated radially compressible plastic tube extending distally from the coaxially movable means, coaxially about the guidewire through the O-ring and a substantial portion of the lumen. This tube serves to better facilitate the seal between the O-ring and the guidewire.

BRIEF DESCRIPTION OF THE DRAWING

FIG. 1 shows a catheter guidewire assembly that includes the proximal end fitting of the invention.

FIG. 2 is an enlarged sectional view of the proximal end fitting.

FIG. 3 is a view of a prior art proximal end fitting.

FIG. 4 is a table of the test results of the proximal end fitting of the invention.

Like parts in the assemblies shown in the figures bear the same reference numerals.

MODES FOR CARRYING OUT THE INVENTION

FIGS. 1 and 2 illustrate the preferred embodiment of the proximal end fitting of the invention.

FIG. 1 depicts the entire catheter guidewire assembly. The assembly includes the guidewire 11, the catheter 12 and the proximal end fitting 13. As shown in FIG. 1, the guidewire is a flexible torqueable wire having an overall length of between about 70–300 cm between its proximal and distal ends (14 and 15, respectively) and a maximum outer diameter of between about 0.2 mm and 1.0 mm. Distal portion 15 of guidewire 11 is fully or partially encased in a soft flexible sleeve.

As further shown in FIG. 1, the catheter includes an elongated tubular member 19 having proximal and distal ends 20 and 21, respectively. The tubular member is preferably between about 50–300 cm in length and typically between about 100–200 cm in length. Catheter 12 includes a relatively stiff proximal segment 22 and a relatively more flexible distal segment 23 with a segment 24 between the proximal and distal ends composed of the overlapping coaxial tubes of the proximal and distal segments.

Proximal end 27 of catheter 12 is sealingly attached to the distal portion 15 of proximal end fitting 13. As shown in FIG. 2, the proximal end fitting comprises a tubular body 28 having a proximal and distal end 29 and 30, respectively, and a lumen 31 extending between the two ends. The lumen has an overall length of between about 2 and 10 cm, more preferably between about 4 and 6 cm and most preferably about 5 cm. The inner diameter of the lumen is between about 2.0 and 4.0 mm, more preferably between about 2.20 and 2.25 mm and most preferably about 2.25 mm. The outer diameter of the lumen is between about 4 and 8 mm, more preferably between about 5 and 6 mm and most preferably 5.5 mm.

A side port 32 may be included in proximal end fitting 13 in order to allow for the introduction of fluid material into the catheter lumen 33. Such materials include radio-opaque agents for viewing blood vessel anatomy and blood flow characteristics in the target region; vaso-occlusive agents, such as suspensions of collagen fibers which can be used to produce small-artery vaso-occlusion in the tissue region supplied by the target vessel; and pharmacological agents, such as antitumor drugs which are effective against identified disease states at the target site.

Further embodiments of the above described catheter guidewire assembly are described in U.S. Pat. No. 4,955,862 which is herein incorporated by reference in its entirety.

Proximal end fitting 13 of the present invention further comprises an axially movable means that can be received within the proximal end 29 of the tubular body 28. An elongated radially compressible tube 37 extends distally from the axially movable means coaxially about guidewire 11 through O-ring 38 to facilitate the seal between the guidewire and the O-ring. The O-ring may be positioned anywhere within the proximal end of the lumen proximal to the side port such that when the O-ring is compressed a seal will be created about the guidewire to avoid reflux of fluid. In the preferred embodiment depicted in FIGS. 1 and 2, the O-ring is positioned at the distal end of the threaded portion of proximal end fitting 13 such that when the axially movable means 10 is threadedly connected to the proximal end fitting, compression of O-ring 38 results.

In the preferred embodiment depicted in FIGS. 1 and 2, the axially movable means comprises an end cap 36. The end cap comprises a central shaft 39 through which lumen compressible tube 37 is attached. The method of construction of the compressible tube is described below. A first collar 40 concentrically surrounds central tubular shaft 39. This collar has a smooth outer surface and a threaded inner surface such that when end cap 36 is axially rotated, the threads on the collar connect with threads on the outer surface of the proximal end of tubular body 28.

A second collar 41 concentrically surrounds first collar 40 and central tubular shaft 39. This collar has a smooth inner surface and an outer surface with ribs 42. These ribs allow for ease in gripping the end cap so that the end cap can be rotated and threadedly attached to tubular body 36.

RADIALLY COMPRESSIBLE TUBE CONSTRUCTION

A wire mandrel with an outside diameter of 0.38 mm is placed inside a polypropylene tube with an inside diameter of 0.46 mm and an outside diameter of 0.76 mm that is approximately 12 cm long to form a wire mandrel and polypropylene tube assembly. The wire mandrel and polypropylene tube assembly is then inserted into a heat-shrink polyethylene tube expanded to about 2.54 mm inside diameter with a wall thickness of about 0.051 mm. The entire assembly is heated to the melting point (approximately 200° C.) of the polypropylene tubing. The heat-shrink tube will cause the polypropylene to collapse over the mandrel and have a precise inside diameter. The mandrel is removed when the material is cooled. In the preferred embodiment of the present invention, the polymer tube is trimmed to about 10 cm in length such that the tube coaxially surrounds the guidewire to a point just beyond where proximal end 27 of catheter 12 is attached to distal end 15 of proximal end fitting 13. The polymer tube may be trimmed to any convenient length such that it aids in sealingly connecting the O-ring and the guidewire.

TEST CHARACTERISTICS

A Tracker 25 catheter (Target Therapeutics, Inc., San Jose, Calif.) equipped with a 0.36 mm Seeker guidewire (Target Therapeutics, Inc.) and the proximal end fitting of the invention is filled with 30 percent contrast medium. The guidewire is positioned so that the wire is about 10 cm from the tip of the catheter. The tip of the catheter is sealed using a hemostat. The compressible plastic tube (37 in the drawings) is positioned over the wire in such a manner that part of the tube can be captured by the O-ring seal of the fitting. An indeflator filled with contrast medium is attached to the side port of the fitting. The O-ring seal of the fitting is tightened slightly to capture the compressible tube. The guidewire is checked for movement. Air is vented from the system. Pressure is then applied on the indeflator for one minute at 10 psi. The end of the compressible tube was checked for leakage. The applied pressure was increased at 10 psi increments up to 120 psi. Ten samples were tested. The results are shown in FIG. 4. (In FIG. 4, "n.l." means "no leakage.")

Using the same assembly described, with no pressure applied to the system, the ring seal was compressed until the guidewire was captured. After five minutes, the ring seal was released and the guidewire checked for movement. The procedure was repeated ten times. Ten samples were tested. Wire movement was not effected under any conditions tested.

Modifications of the above-described modes for carrying out the invention that are obvious to persons of skill in the mechanical, surgical instrument, and catheter/guidewire arts or related fields are intended to be within the scope of the following claims.

I claim:

1. In a proximal end fitting for a catheter guidewire assembly, said assembly comprising a catheter, a guide wire and a proximal end fitting, said proximal end fitting comprising:
   (a) a tubular body having a proximal end and a distal end and a lumen extending between said ends through which the guidewire of said assembly extends;
   (b) means at said distal end for sealingly receiving the proximal end of the catheter of said assembly;
   (c) a compressible O-ring positioned within the lumen; and
   (d) axially movable means received within the proximal end of the body for compressing the O-ring to form a seal about the guidewire;
   the improvement to the proximal end fitting comprising an elongated radially compressible plastic tube extending distally form (d) coaxially about the guide wire through said O-ring and a substantial portion of said lumen, said plastic tube facilitating said seal.

2. The proximal end fitting of claim 1 wherein the axially movable means comprises an end cap with a threaded connection and the proximal end of the body comprises a threaded connection such that the threaded connection at the proximal end of the body is sealingly received within the threaded end cap.

3. The proximal end fitting of claim 2 wherein the end cap further comprises a central tubular shaft with a lumen, through which lumen the elongated radially compressible plastic tube is attached, a first collar concentrically surrounding the central tubular shaft with a smooth outer surface and a threaded inner surface to sealingly receive the threaded proximal end of the body, and a second collar concentrically surrounding said central tubular shaft and said first collar with a smooth inner surface and a ribbed outer surface for gripping the end cap.

4. The proximal end fitting of claim 3 wherein the O-ring is positioned at the proximal end of the tubular body lumen such that when the end cap is threadedly connected to the proximal end of the tubular body, the O-ring is sealingly compressed about the plastic tube.

5. The proximal end fitting of claim 1 wherein the tubular body lumen has an overall length of between about 4 and 6 cm, an inner diameter of between about 0.38 and 0.39 mm and an outer diameter of between about 1.4 and 1.6 mm.

6. The proximal end fitting of claim 4 wherein the outer diameter of the radially compressible plastic tube is such as to facilitate a seal between the tube and the O-ring when the end cap is threadedly connected to the proximal end of the tubular body.

7. The proximal end fitting of claim 1 which further comprises a side port for the introduction of fluid material.

8. The proximal end fitting of claim 1 wherein the elongated radially compressible tube comprises an inner layer of polypropylene and an outer layer of polyethylene.

* * * * *